(12) United States Patent
Bode et al.

(10) Patent No.: US 7,507,984 B2
(45) Date of Patent: Mar. 24, 2009

(54) STORAGE PHOSPHOR LAYER AND SYSTEM AND METHOD FOR ERASING SAME

(75) Inventors: Andreas Bode, Munich (DE); Georg Reiser, Munich (DE); Marc Weber, Munich (DE); Ralph Thoma, Augsburg (DE); Stefan Stallmeister, Gionn (DE); Stephan Baunach, Munich (DE); Heike Minwegen, Bad Aibling (DE); Robert Fasbender, Erlangen (DE); Rupert Dedler, Jengen-Weinhausen (DE)

(73) Assignee: Agfa HealthCare N.V., Mortsel (BE)

( * ) Notice: Subject to any disclaimer, the term of this patent is extended or adjusted under 35 U.S.C. 154(b) by 0 days.

(21) Appl. No.: 11/831,224

(22) Filed: Jul. 31, 2007

(65) Prior Publication Data

US 2008/0054202 A1   Mar. 6, 2008

(30) Foreign Application Priority Data

Aug. 31, 2006   (EP)   .................................. 06119938
Dec. 6, 2006   (EP)   .................................. 06125512

(51) Int. Cl.
  *G01N 23/04*   (2006.01)
(52) U.S. Cl. ...................................... 250/588
(58) Field of Classification Search ............... 250/484.4, 250/588
  See application file for complete search history.

(56) References Cited

U.S. PATENT DOCUMENTS 4,202,600 A * 5/1980 Burke et al. ................. 359/514
4,786,808 A 11/1988 Saito
4,849,633 A 7/1989 Yamada et al.
5,065,021 A * 11/1991 Arakawa ..................... 250/588
5,534,709 A 7/1996 Yoshimoto et al.

(Continued)

FOREIGN PATENT DOCUMENTS

EP   0 704 716 A1   4/1996

(Continued)

OTHER PUBLICATIONS

International Search Report from EP06119938.6, filed Aug. 31, 2006.

(Continued)

*Primary Examiner*—David P Porta
*Assistant Examiner*—Kiho Kim
(74) *Attorney, Agent, or Firm*—Houston Eliseeva, LLP (57) ABSTRACT

An apparatus (1) for erasing a storage phosphor layer (2) with a holding plane (7) in which the storage phosphor layer (2) lies or can be moved, a radiation source (8, 9, 10) for irradiating the storage phosphor layer (2) with erasing radiation which is suitable for erasing the storage phosphor layer (2), and a reflector (11; 29, 30) for reflecting erasing radiation in the direction of the holding plane (7). In order to increase the erasing efficiency, provision is made such that the reflector (11; 29, 30) is arranged and/or designed such that it reflects erasing radiation, which is reflected by the storage phosphor layer (2), in the direction of the storage phosphor layer (2), and the radiation source (8, 9, 10) is disposed on a base (33; 48, 49), the base (33; 48, 49) being disposed closer to the holding plane (7) than at least part of the reflector (11; 29, 30).

26 Claims, 5 Drawing Sheets

U.S. PATENT DOCUMENTS

| | | |
|---|---|---|
| 6,369,402 B1 | 4/2002 | Gebele et al. |
| 6,373,074 B1 | 4/2002 | Mueller et al. |
| 6,528,812 B1 | 3/2003 | Leblans et al. |
| 6,642,535 B2 | 11/2003 | Gebele et al. |
| 6,762,882 B2 | 7/2004 | Melzer et al. |
| 6,858,861 B2 | 2/2005 | Gebele et al. |
| 6,897,994 B2 | 5/2005 | Thoma et al. |
| 7,071,484 B2 | 7/2006 | Lind et al. |
| 7,075,200 B2 | 7/2006 | Minato et al. |
| 7,109,496 B2 | 9/2006 | Gebele et al. |
| 7,122,822 B2 | 10/2006 | Bode et al. |
| 7,151,272 B2 | 12/2006 | Nitsche et al. |
| 7,170,079 B2 | 1/2007 | Fasbender et al. |
| 7,170,080 B2 | 1/2007 | Fasbender et al. |
| 7,176,476 B2 | 2/2007 | Lind et al. |
| 7,227,167 B2 | 6/2007 | Leblans et al. |
| 2003/0123613 A1 | 7/2003 | Evans et al. |
| 2004/0004843 A1 | 1/2004 | Melzer et al. |
| 2004/0007676 A1 * | 1/2004 | Iwabuchi et al. ......... 250/484.4 |
| 2004/0130768 A1 | 7/2004 | Thoma et al. |
| 2004/0208639 A1 | 10/2004 | Melzer et al. |
| 2004/0232365 A1 | 11/2004 | Reiser et al. |
| 2004/0238765 A1 | 12/2004 | Bode et al. |
| 2004/0239998 A1 | 12/2004 | Reiser |
| 2005/0012057 A1 | 1/2005 | Smith et al. |
| 2005/0017207 A1 | 1/2005 | Trzcinski et al. |
| 2006/0022157 A1 | 2/2006 | Reiser |
| 2006/0145104 A1 * | 7/2006 | Rogers et al. ............... 250/588 |
| 2006/0180773 A1 | 8/2006 | Frankenberger et al. |
| 2006/0180777 A1 | 8/2006 | Frankenberger et al. |
| 2007/0152179 A1 | 7/2007 | Mair et al. |
| 2007/0153975 A1 | 7/2007 | Mair et al. |

FOREIGN PATENT DOCUMENTS

| | | |
|---|---|---|
| EP | 0 964 270 A2 | 12/1999 |
| EP | 1 403 077 A1 | 3/2004 |
| EP | 1 403 695 A1 | 3/2004 |
| EP | 1 503 241 A1 | 2/2005 |
| JP | 2003-186128 | 7/2003 |
| JP | 2005-275075 | 10/2005 |
| JP | 2005275075 A * | 10/2005 |
| WO | 01/50960 A2 | 7/2001 |

OTHER PUBLICATIONS

International Search Report from EP06125512.1, filed Dec. 6, 2006.
European Search Report from EP06119939.4, filed on Aug. 31, 2006.

* cited by examiner

STORAGE PHOSPHOR LAYER AND SYSTEM AND METHOD FOR ERASING SAME

RELATED APPLICATIONS

This application claims priority to European Patent Application Nos. EP06119938.6 filed on Aug. 31, 2006 and EP06125512.1, filed on Dec. 6, 2006, both of which are incorporated herein by reference in their entirety.

This application relates to U.S. Application Publication No. US 2008/0054200 A1, published on Mar. 6, 2008 titled "Storage Phosphor Layer and System and Method for Erasing Same," by Dr. Andreas Bode et al., and U.S. Application Publication No. US 2008/0054201 A1, published on Mar. 6, 2008titled, "Storage Phosphor Layer and System and Method for Erasing Same," by Dr. Andreas Bode et al.

BACKGROUND OF THE INVENTION

Apparatuses for erasing a storage phosphor layer are used in particular in the field of computer radiography (CR) for medical purposes. A picture is produced of an object, for example a patient or a body part of the patient, by means of X-ray radiation which is stored in a storage phosphor layer as a latent picture. Therefore, this type of X-ray picture contains X-ray information about the object. In order to read out the X-ray information stored in the storage phosphor layer, the storage phosphor layer is stimulated by means of an irradiation device. As a result of this stimulation, the storage phosphor layer emits radiation which has an intensity corresponding to the X-ray information stored in the storage phosphor layer. The radiation emitted by the storage phosphor layer is collected by a detection device and converted into electrical signals, which contain an image of the X-ray information. The electrical signals are further processed and the X-ray information stored in the storage phosphor layer is then made visible. The X-ray information can be displayed directly on a monitor, for example, or be written onto a photographic X-ray film by means of a printer used especially for X-ray pictures.

After reading out the X-ray information from the storage phosphor layer, remains of the latent picture remain in the latter. Furthermore, noise information can be stored in the layer. In order to be able to use the storage phosphor layer for further X-rays, it is therefore erased. For this procedure, a radiation source is used that emits erasing radiation onto the storage phosphor layer. An apparatus for erasing a storage phosphor layer is known from U.S. Pat. No. 7,075,200 B2. As a radiation source this erasing apparatus contains two lines with light emitting diodes, disposed parallel to one another, for emitting the erasing radiation and which are disposed on cooling elements made of aluminum. For erasure, the storage phosphor layer is pushed in a direction of conveyance through a ray path of the lines of light emitting diodes. The two lines of light emitting diodes are integrated into reflectors which are spaced apart from one another. The reflectors serve to reflect erasing radiation emitted by the light emitting diodes in the direction of the storage phosphor layer. The reflectors are respectively formed by means of two reflector surfaces which are disposed to either side of the lines of light emitting diodes in the direction of conveyance. The reflector surfaces adjoin the cooling elements with obtuse inner angles so that the reflectors open from the cooling elements in the direction of the storage phosphor layer.

SUMMARY OF THE INVENTION

It is the object of the present invention to enable high efficiency when erasing a storage phosphor layer.

With the apparatus according to the invention provision is made such that the reflector is arranged and/or designed such that it reflects back erasing radiation which is reflected by the storage phosphor layer in the direction of the storage phosphor layer, and the radiation source is disposed on a base, the base being disposed closer to the holding plane than at least part of the reflector. The system according to the invention includes the apparatus according to the invention and a storage phosphor layer.

The knowledge which forms the basis of the invention is that the storage phosphor layer has a high degree of reflection due to which a large part of the erasing radiation with which the storage phosphor layer is irradiated is reflected by the latter without being used and so does not contribute to the erasure of undesired picture information stored in the storage phosphor layer.

According to the invention, the erasing radiation reflected by the storage phosphor layer is captured by the reflector and reflected back again in the direction of the storage phosphor layer. This reflection can be directed (specular) or diffuse. In this regard, the reflector is designed with an appropriate shape and size and/or is an appropriate distance away from the storage phosphor layer.

The erasing radiation reflected back by the reflector can therefore also contribute to erasure of the storage phosphor layer. In this way, the efficiency of the erasure is substantially improved. Furthermore, the power requirement is less, and this leads to less lost heat and an increase in lifespan.

Due to the positioning of the radiation source on a base according to the invention, it is moreover guaranteed that very little of the erasing radiation reflected by the reflector, and which has already previously been reflected by the storage phosphor layer in the direction of the reflector, is reflected by the reflector into the radiation source. In this way undesired reabsorption of erasing radiation, which is reflected by the storage phosphor layer and by the reflector, in the radiation source is avoided, and so efficiency losses are greatly reduced.

The base is preferably a component part of the reflector and is formed by raising the reflector in the direction of the holding plane. Preferably, the reflector is formed together with the base from one piece, in particular a reflective metal sheet. The actual reflector surfaces of the reflector advantageously adjoin the base directly here.

Advantageously, the radiation source has a plurality of individual light sources, such as e.g. light emitting diodes, which are disposed in a radiation plane that extends parallel to the holding plane.

In one advantageous embodiment of the invention, the base is formed, reflectively, on the side facing towards the holding plane. In this way, it can be guaranteed that the base also reflects erasing radiation that reflected by the storage phosphor layer back in the direction of the storage phosphor layer. This further increases the efficiency when erasing the storage phosphor layer.

In a further advantageous embodiment, the base is in particular curved in form in the direction of the holding plane. In relation to the holding plane, the base is convex in form. In one particularly preferred embodiment of the invention, the base has at least one indentation in which the radiation source is formed. Particularly advantageously, the base is disposed closer than the whole reflector to the holding plane. These advantageous embodiments enable particularly good protection of the radiation source from erasing radiation reflected by the reflector taken individually and in particular as a whole.

Preferably, the reflector has a reflector surface curving away from the holding plane. In relation to the holding plane, the reflector is concave in form. In this way the reflected erasing radiation, particularly well directed in the direction of the storage phosphor layer, can be reflected without hitting the radiation source.

In one advantageous embodiment of the invention, the reflector has a flat reflector surface that extends in particular parallel to the holding plane. This type of reflector form can reliably collect reflected erasing radiation and reflect it back to the storage phosphor layer. This form of reflector can be manufactured inexpensively and can be compact in design.

In a further advantageous embodiment, the reflector has a reflector surface with a structure. With this type of structure the efficiency of the erasure can be even further increased. The structure can in particular be fluted, or in the form of a roof or saw teeth and/or triangular etc.

In one particularly preferred embodiment of the invention, the structured reflector surface is retroreflective in form so that it reflects back at least part of the erasing radiation to points of the storage phosphor layer at which it was previously reflected by the storage phosphor layer. This type of retroreflective reflector surface guarantees particularly even erasure of the storage phosphor layer. At those points that have reflected a lot of erasing radiation, a lot of erasing radiation is also reflected back. The retroreflective reflector surface can in particular be designed in the form of a so-called "cat's eye", and be inserted as a film. This is particularly space saving and cost-effective.

Particularly preferably, a drive for producing a relative movement between the holding plane and the radiation source is provided. This simply enables even production of the relative movement and efficient erasure of the storage phosphor layer.

Particularly advantageously, the reflector has at least two reflector surfaces so that the reflector, considered in the direction of the relative movement, is formed to either side of the radiation source. In this way, a particularly large amount of erasing radiation can be collected and reflected back.

In one particularly preferred embodiment of the invention, the reflector is formed mirror- or reflective- symmetrically in the direction of the relative movement, an axis of symmetry extending at right angles to the direction of the relative movement, and considered in the direction of the relative movement, centrally through the radiation source. By means of this type of reflector a large quantity of reflected erasing radiation can be collected to both sides of the radiation source and be reflected back to the storage phosphor layer.

In one advantageous embodiment of the invention, a width of the reflector in the direction of the relative movement is at least ten times as great as a smallest distance between the reflector and the holding plane. By means of this dimensioning of the reflector with a large width in the direction of the relative movement and a small distance from the holding plane, it can in particular be guaranteed for the storage phosphor layer that a large part of erasing radiation reflected or dispersed by the storage phosphor layer can be captured or collected and reflected back again in the direction of the storage phosphor layer.

Particularly advantageously, the radiation source has at least two lines with light emitting diodes extending at right angles to the direction of the relative movement and parallel to the holding plane. In this way, a sufficiently high intensity of erasing radiation can be produced, the power consumption of the light emitting diodes being particularly low.

Preferably, the at least two lines with light emitting diodes are integrated into the base. A distance between the at least two lines is smaller than or equal to a distance between the light emitting diodes and the holding plane. Due to this, the erasing apparatus can be particularly compact in design. Furthermore, the erasing radiation emitted by the lines of light emitting diodes can be emitted, particularly well directed, to the storage phosphor layer.

Particularly preferably, a separate reflector and a separate base are respectively allocated to the at least two lines with light emitting diodes. The light emitting diodes of the respective lines further emit radiation, in particular in a narrow-band wavelength range different to that of the light emitting diodes of the other lines. The reflectors are designed in particular so that they contribute to separation of the erasing radiation with the different wavelength ranges emitted by the different lines of light emitting diodes. In this way particular spectral ranges can be prevented from mutually effecting or disrupting one another. The wavelength ranges can advantageously be chosen such that wavelengths which do not contribute to the erasure of the type of storage phosphor layer used are not available. Due to this, the filtering out of these wavelengths, which would otherwise be necessary, is not necessary. Furthermore, particularly good erasing efficiency is achieved.

Preferably, the at least two lines with light emitting diodes are disposed one behind the other in the direction of the relative movement such that when implementing the relative movement in order to erase the storage phosphor layer, short wavelength or shortwave erasing radiation hits the storage phosphor layer before long wavelength or longwave erasing radiation. In particular here, blue erasing radiation is directed at the storage phosphor layer before red erasing radiation. In this way particularly good erasing efficiency is guaranteed.

Preferably, an intensity of the longwave erasing radiation is greater than an intensity of the shortwave erasing radiation. In particular, a ratio of blue to red erasing radiation can be chosen such that 66% of the erasing radiation is red and 33% of the erasing radiation is blue erasing radiation. This guarantees even better erasing efficiency.

Particularly preferably, a further reflecting surface positioned opposite the reflector, as considered in the direction at right angles to the direction of the relative movement, is provided for reflecting erasing radiation. The further reflecting surface is formed such that it reflects the erasing radiation directionally (specularly) or diffusely, in one example. Advantageously, by means of this further reflecting surface, at the start and/or at the end of the erasing process, i.e. when the ray path of the radiation source is not or not fully directed at the storage phosphor layer, the erasing radiation emitted by the radiation source can be reflected by the further reflecting surface in the direction of the reflector. The erasing radiation reflected by the further reflecting surface and which in particular has not yet reached the storage phosphor layer, can therefore be directed by the reflector towards the storage phosphor layer. In particular, the front and, if appropriate, the rear edge of the storage phosphor layer can therefore be erased with a high level of efficiency.

Preferably, the further reflecting surface is disposed on the side of the holding plane facing away from the reflector. In this way, it can be particularly well guaranteed that erasing radiation not hitting the storage phosphor layer is reflected by the further reflecting surface so as to then be reflected by the reflector in the direction of the storage phosphor layer.

Preferably, front surfaces and/or side surfaces of the reflector are reflective in design. In this way, erasing radiation reflected by the storage phosphor layer can be collected even better and more efficiently and be reflected back in the direction of the storage phosphor layer.

Preferably, the storage phosphor layer of the system according to the invention has a degree of reflection for the erasing radiation of greater than or equal to 70%, and in particular greater than or equal to 80%. The erasing apparatus according to the invention can be used particularly efficiently for storage phosphor layers with this high level of reflection.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
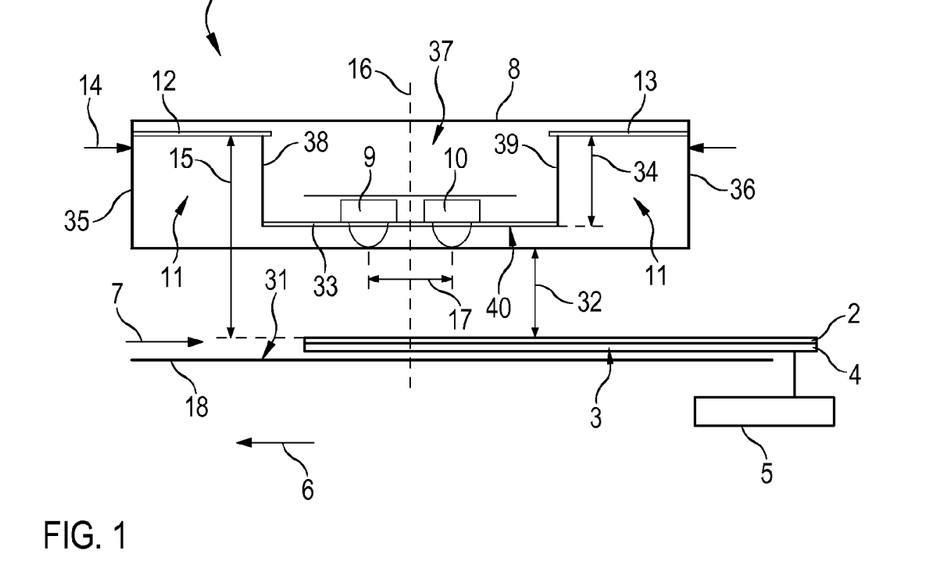
FIG. 1 shows a first exemplary embodiment of an erasing apparatus according to the invention with a reflector which has flat reflector surfaces extending parallel to a storage phosphor layer, and with a further reflection surface positioned opposite the reflector.

FIG. 1 shows a first exemplary embodiment of an erasing apparatus 1 which has been constructed according to the principles of the present invention for erasing X-ray information which is stored in a storage phosphor layer 2 of a storage phosphor plate 3. The storage phosphor plate 3 has a carrying layer 4 on which the storage phosphor layer 2 is placed. The storage phosphor layer 2 is preferably made up of a plurality of storage phosphor particles which serve to store the X-ray information. The carrying layer 4 is preferably 1-2 millimeters (mm) thick. Here, the storage phosphor plate 3 does not form part of the erasing apparatus 1, but is pushed or inserted into the erasing apparatus 1 from the outside, in one example. Within the erasing apparatus 1, the storage phosphor plate 3 is moved by means of a drive 5 in a direction of conveyance 6, which is represented by an arrow. The storage phosphor plate 3 is moved within the erasing apparatus 1 in a holding plane 7 and can be moved within this holding plane 7. Below the holding plane 7, there is a support 18 on which the storage phosphor plate 3 lies and be moveably guided.

The erasing apparatus 1 contains a radiation source 8 for emitting erasing radiation. The radiation source 8 here has two lines of light emitting diodes 9 and 10 disposed parallel to one another. The lines of light emitting diodes 9, 10 each contain a plurality of light emitting diodes disposed next to one another. The lines of light emitting diodes 9, 10 extend over the whole length of the storage phosphor layer 2. In the illustration according to FIG. 1, the length of the storage phosphor layer 2 extends at right angles to the direction of conveyance 6 and in the direction of the plane of the drawing sheet. The width of the storage phosphor layer 2 extends in the direction of conveyance 6. The lines of light emitting diodes 9, 10 are disposed on a level base 33 that extends parallel to the holding plane 7. By means of the drive 5, the storage phosphor layer 2 is conveyed past the lines of light emitting diodes 9, 10 with even conveyance speed in the direction of conveyance 6. In this way, the storage phosphor layer 2 passes through the ray paths of the lines of light emitting diodes 9, 10. Alternatively, it is also possible to convey the radiation source instead of the storage phosphor plate 3, the storage phosphor plate 3 is then not moved in the erasing apparatus 1. In both cases, a relative movement is implemented between the radiation source 8 and the storage phosphor layer 2 lying in the holding plane 7, which here extends in the direction of the arrow for the direction of conveyance 6.

When conveying the storage phosphor plate 3, the erasing light emitted by the light emitting diodes of the lines of light emitting diodes 9, 10 hits the storage phosphor layer 2. Part of the erasing light penetrates into the storage phosphor layer 2 and erases the X-ray information remaining in the latter following a read-out and, if applicable, any noise which is present. Since the storage phosphor layer 2 has a degree of reflection of at least 70%, and in particular of at least 80% for the erasing light, a large part of the erasing light is reflected by the storage phosphor layer 2, without contributing to the erasure.

In order to achieve a high level of efficiency and a high degree of effectiveness when erasing, the erasing apparatus 1 has a reflector 11. In the present exemplary embodiment, the reflector 11 has two level reflector surfaces 12 and 13 extending parallel to the holding plane 7 and the storage phosphor layer 2. Considered in the direction of conveyance 6, the reflector surfaces 12, 13 are disposed to either side of the base 33 and are advantageously equal in size. However, it is also possible to provide just a single reflector surface on one of the sides of the base 33. Furthermore, it is possible to design one of the two reflector surfaces 12, 13 to be smaller than the other.

According to the invention, the base 33 is disposed closer by a distance 34 to the holding plane 7 than the reflector surfaces 12, 13. In the present first exemplary embodiment the base 33 is therefore disposed closer than the whole reflector 11 with its reflector surfaces 12, 13 to the holding plane 7.

The reflector surfaces 12, 13 are connected to the base 33 by connection surfaces 38 and 39.

The reflector surfaces 12, 13 and the base 33 respectively extend over the whole length of the storage phosphor layer 2. Considered in the direction of conveyance 6 they extend collectively over a width 14 of the radiation source 8. A smallest distance 15 of the reflector 11 with its reflector surfaces 12, 13 is that from the surface of the storage phosphor layer 2 located in the holding plane 7. The width 14 is at least ten times greater than the smallest distance 15.

The radiation source 8 and in particular the reflector 11 are mirror-symmetrical in form in the direction of conveyance 6. Here, an axis of symmetry 16 extends at right angles to the direction of conveyance 6, and in relation to the width 14, centrally through the radiation source 8. In the present exemplary embodiment the axis of symmetry 16 therefore extends between the two lines of light emitting diodes 9, 10.

The two lines of light emitting diodes 9, 10 are integrated centrally into the base 33 here. A distance 17 between the two lines of light emitting diodes 9, 10 is advantageously smaller than or equal to a distance 32 between the light emitting diodes and the storage phosphor layer 2 lying in the holding plane 7.

On their surfaces facing towards the storage phosphor layer 2, the reflector surfaces 12, 13 have reflecting layers which are highly reflective for erasing light reflected by the storage phosphor layer 2. The same applies in the present exemplary embodiment to the base 33 which is provided with a reflective layer 40 on its surface facing in the direction of the holding plane 7, and the connection surfaces 38, 39. By means of these reflective layers of the reflector surfaces 12, 13 and the base 33, erasing light, which is reflected or dispersed by the storage phosphor layer 2, is reflected back in the direction of the storage phosphor layer 2. Due to this re-reflection, it is possible for the erasing light to now penetrate into the storage phosphor layer 2 in order to erase the X-ray information.

On its front face side, as considered in the direction of conveyance 6, the radiation source 8 includes a reflection surface 35, and on its rear face side, as considered in the direction of conveyance 6, a reflection surface 36. On its side edges the radiation source has further reflection surfaces of which a further reflection surface 37 is shown in FIG. 1. The face-side and side reflection surface 35-37 include reflective layers, in particular on their inwardly facing surfaces.

The individual light emitting diodes 9, 10 have a housing which, in the exemplary embodiment of FIG. 1 shown, is characterized by a rectangular cross-section. On the housing, there is a transparent region for the emitted erasing light which is shown in the illustrated example by a round dome. A light-emitting semiconductor is disposed between the housing and the transparent region. The individual light emitting diodes 9, 10 are preferably attached to the base 33 so that, on one hand, the housing of the light emitting diodes 10 is covered by the reflective layer 40 located on the base 33 from the side facing towards the storage phosphor layer 2, and, on the other hand, the light-emitting semiconductor lies above the reflective layer 40, i.e. on the side facing towards the storage phosphor layer 2. In this way a high light output of the light emitting diodes 9, 10 is achieved with at the same time a high level of re-reflection of the erasing light reflected by the storage phosphor layer 2.

The erasing apparatus 1 has a further reflection surface 31 which is positioned opposite the reflector surfaces 12, 13 and the base 33, as considered in a direction at right angles to the direction of conveyance 6. The reflection surface 31 is designed to reflect erasing light that has been emitted by the radiation source 8. If applicable, further erasing light reflected by the reflection surface 31 has furthermore already been reflected by the storage phosphor layer 2, the reflector surfaces 12, 13 and/or the base 33. In order to reflect erasing light, the reflection surface 31 is in particular placed on the side of the support 18 facing towards the radiation source 8, i.e. on the side of the holding plane 7 facing away from the reflector 11. The reflection surface 31 is advantageously applied to the support 18 as a thin layer. The reflection surface 31 is therefore arranged such that the storage phosphor plate 3 is conveyed between the radiation source 8 and the reflection surface 31. The reflection surface 31 reflects the erasing light to the reflector 11 directionally (specularly) or diffusely. Here, the reflection surface 31 is advantageously as wide in the direction of conveyance 6 as the reflector 11 with its reflector surfaces 12, 13 and the base 33. In this way, it can advantageously be guaranteed that forms of the reflection surface 31 and the reflector 11 and the base 33 correspond particularly well to one another. A particularly large quantity of erasing radiation that is emitted by the radiation source 8 is reflected by the reflection surface 31 and a large quantity of this reflected erasing radiation is reflected by the reflector 11 and the layer 40 of the base 33 in the direction of the storage phosphor layer 2. In this way, particularly good erasing efficiency is achieved. FIG. 1 shows the storage phosphor plate 3 inserted into the erasing apparatus 1. Advantageously, the reflection surface 31 guarantees that the erasing light emitted by the radiation source 8 then also contributes to the erasure with a high degree of effectiveness if the storage phosphor plate 3 is still not fully located within the erasing apparatus 1. In particular, it is guaranteed that the leading edge of the storage phosphor layer 2 is erased with increased efficiency. The same applies when the storage phosphor plate 3 is drawn out of the erasing apparatus 1. For erasing the storage phosphor layer 2m it is alternatively possible to leave the storage phosphor plate 3 in the erasing apparatus 1 and to convey the radiation source 8 together with the reflector 11 and the reflection layer 31 positioned opposite along the storage phosphor plate 3.

Figure 2:
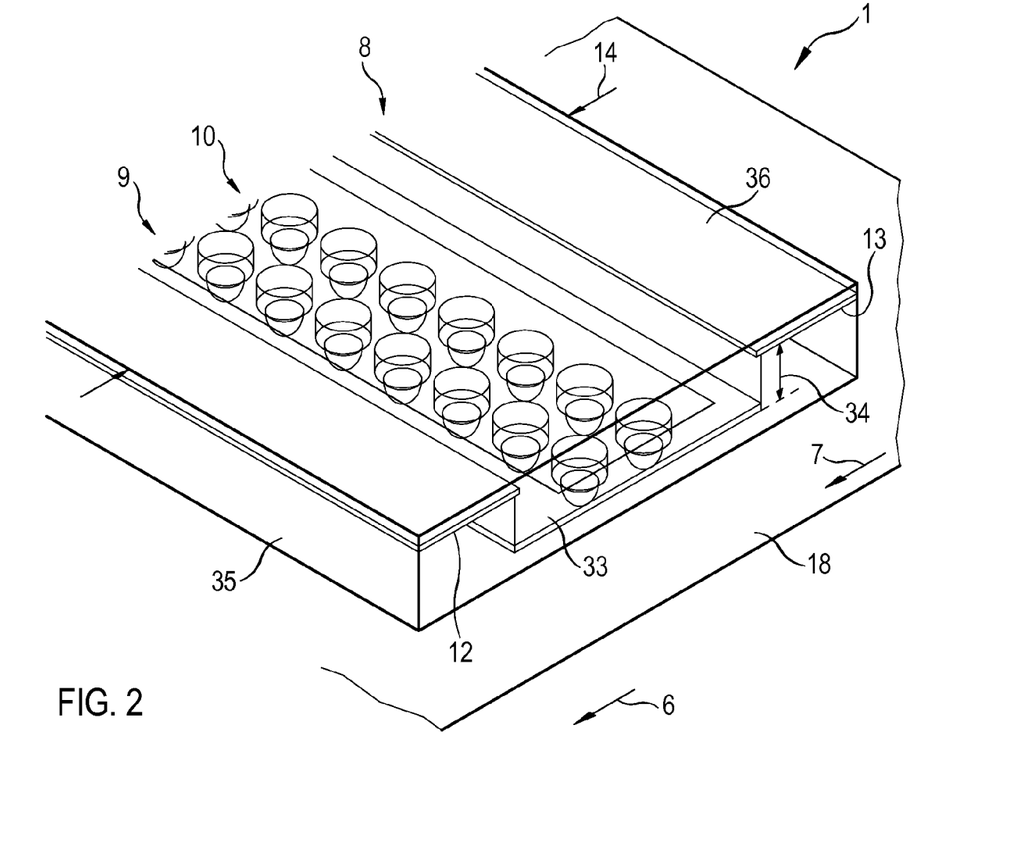
FIG. 2 shows a perspective illustration of the erasing apparatus according to the first exemplary embodiment.

FIG. 2 shows a perspective illustration of part of the erasing apparatus 1 according to FIG. 1 for clarification. One can clearly see the width of the lines of light emitting diodes 9 and 10 in the longitudinal direction of the erasing apparatus 1.

Figure 3:
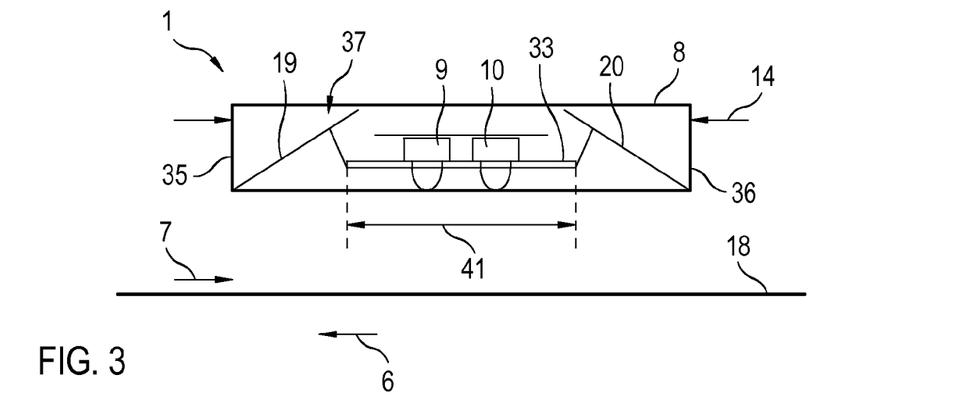
FIG. 3 shows a second exemplary embodiment of the erasing apparatus according to the invention with a reflector which has reflector surfaces with a triangular structure.

FIG. 3 shows a second exemplary embodiment of the erasing apparatus 1 according to the invention. The storage phosphor plate 3 is not shown here. The support 18 is shown over which the holding plane 7 for holding and moving the storage phosphor plate 3 is located. The reflector 11 has two reflector surfaces 19 and 20. The reflector surfaces 19, 20 each have a structure that corresponds substantially to an isosceles triangle. These reflector surfaces 19, 20 structured in a triangular shape are open in the direction of the holding plane 7. The intersection points of the short sides with the long sides of the reflector surfaces 19, 20 are spaced further apart from the holding plane 7 than the base 33 extending parallel to the holding plane 7. Therefore, the base 33 is disposed closer to the holding plane 7 than a part of the reflector 11. In the direction of conveyance 6, the base 33 has a width 41 which is 42 millimeters (mm).

Figure 4:
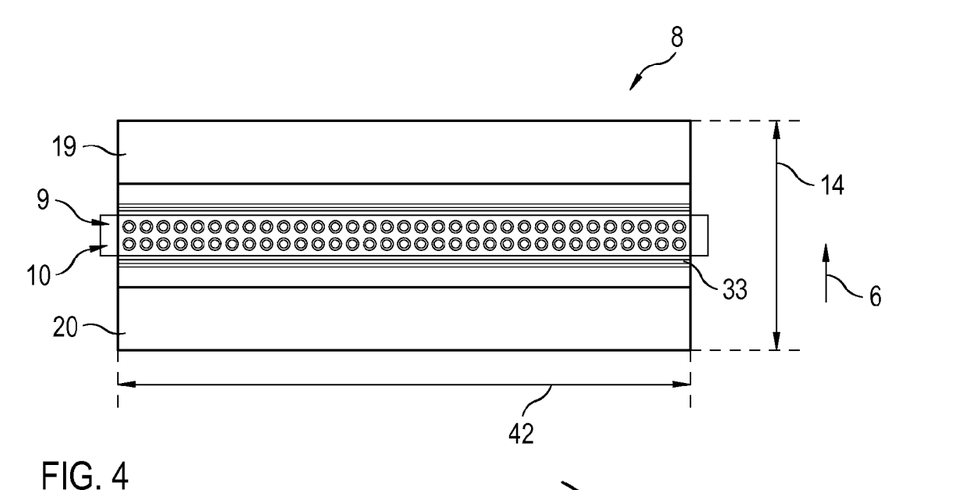
FIG. 4 shows a top view of a lower side of the radiation source of the erasing apparatus according to the second exemplary embodiment.
Figure 5:
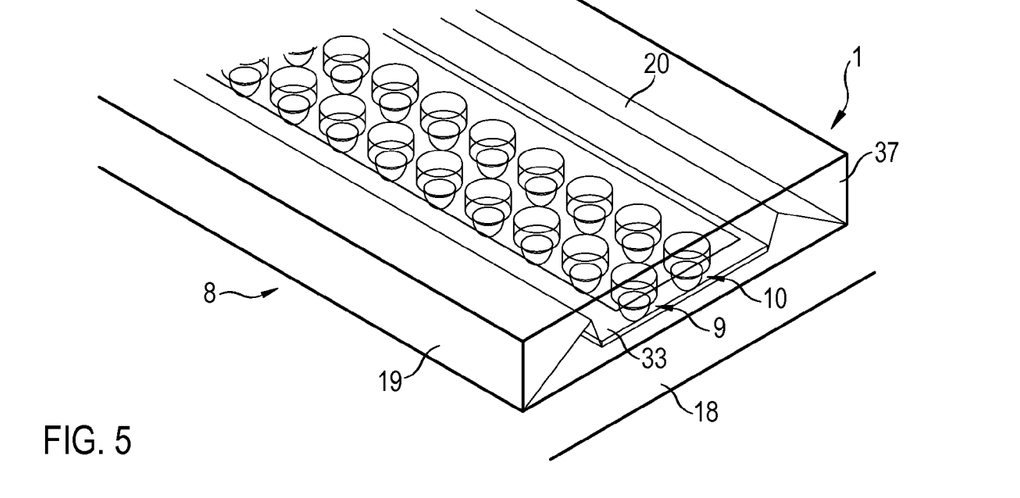
FIG. 5 shows a perspective illustration of the erasing apparatus according to the second exemplary embodiment.

FIG. 4 shows a top view of the lower side of the radiation source 8 according to FIG. 3. One can see the parallel arrangement of the light emitting diodes of the two lines of light emitting diodes 9, 10. The radiation source 8 extends over a length 42, which is at least as great as the longitudinal extension of the storage phosphor layer 2. For further clarification, FIG. 5 shows a perspective illustration of the erasing apparatus 1 according to the second exemplary embodiment according to FIGS. 3 and 4.

Figure 6:
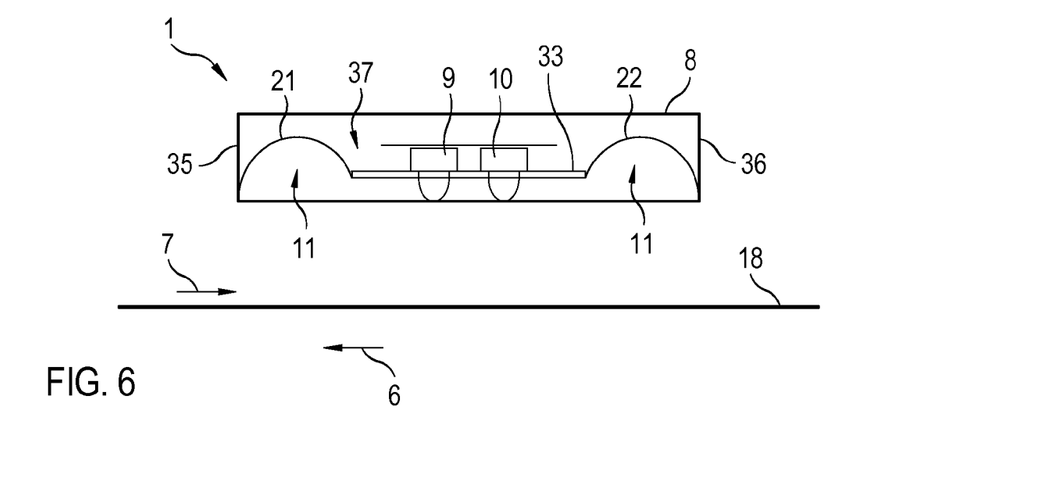
FIG. 6 shows a third exemplary embodiment of the erasing apparatus according to the invention with a groove-shaped reflector which has reflector surfaces curving away from the holding plane for the storage phosphor layer.
Figure 7:
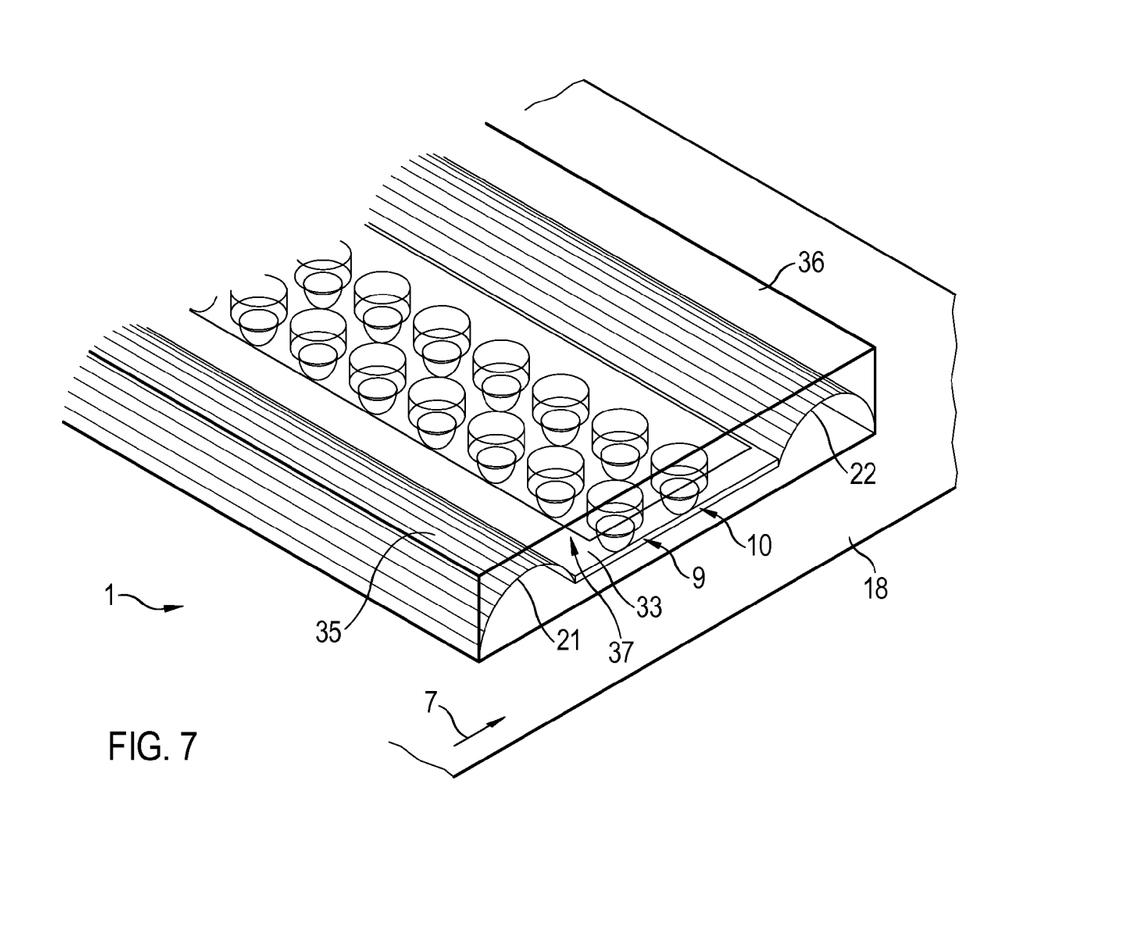
FIG. 7 shows a perspective illustration of the erasing apparatus according to the third exemplary embodiment.

FIG. 6 shows a third exemplary embodiment of the erasing apparatus 1 according to the invention. Here, the radiation source 8 has a reflector 11 with groove-shaped reflector surfaces 21 and 22. These groove-shaped reflector surfaces 21 and 22 are designed such that they curve away, starting at their connection points with the base 33, from the holding plane 7 for the storage phosphor layer 3. In this exemplary embodiment, the base 33 is therefore also closer to the holding plane 7 than a part of the reflector surfaces 21, 22. For further clarification, FIG. 7 shows a perspective illustration of the erasing apparatus 1 according to the third exemplary embodiment according to FIG. 6.

Figure 8:
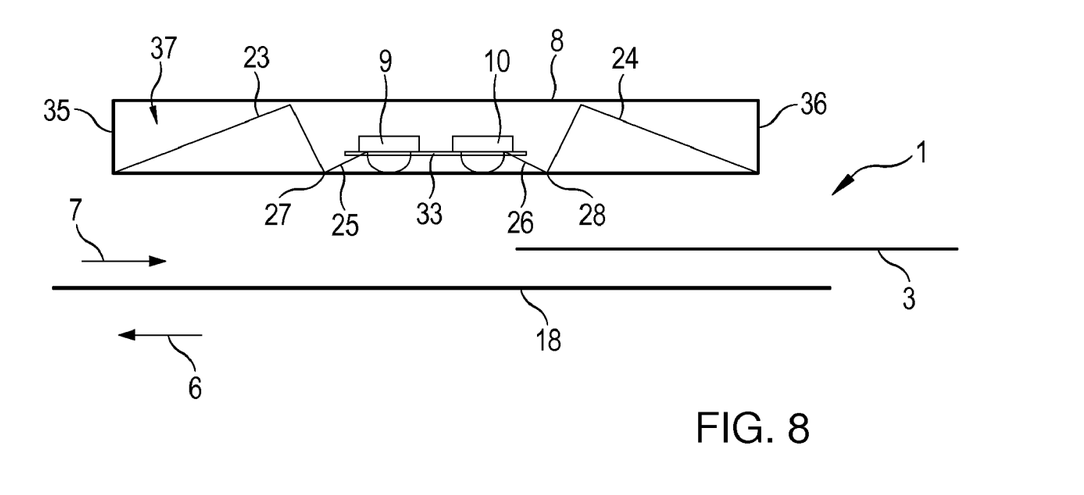
FIG. 8 shows a fourth exemplary embodiment of an erasing apparatus according to the invention with a reflector with triangular-shaped structured reflector surfaces.

FIG. 8 shows a fourth exemplary embodiment of the erasing apparatus 1 according to the invention. In FIG. 8, the storage phosphor plate 3 is shown inserted into the erasing apparatus 1. The base 33, on which the two lines of light emitting diodes 9, 10 are disposed, is offset further from the holding plane 7 in comparison with the second exemplary embodiment according to FIG. 3. The reflector 11 corresponds largely to that of the second exemplary embodiment according to FIG. 3 and has two reflector surfaces 23 and 24, which are disposed to either side of the base 33, as considered in the direction of conveyance 6. The reflector surfaces 23, 24 each have a structure that substantially corresponds to an irregular triangle, as is also the case with the reflector surfaces 19, 20. In addition to this triangular structure, the reflector surfaces 23, 24 have further reflection surfaces 25 and 26. These further reflection surfaces 25, 26 extend at an angle from the holding plane 7 on the nearest edges 27 and 28 of the triangular structure away from the holding plane 7 in the direction of the base 33, and finally hit the latter. In this way connections are established between the reflector surfaces 23, 24 and the base 33. The lines of light emitting diodes 9, 10 are disposed opposite the edges 27, 28 in a type of indentation. In this embodiment therefore, the lines of light emitting diodes 9, 10 are particularly well protected from radiation that is reflected by the reflector surfaces 23, 24 in the direction of the holding plane. However, in this fourth exemplary embodiment too the base 33 is positioned closer to the holding plane 7 than a part of the reflector surfaces 23, 24.

Figure 9:
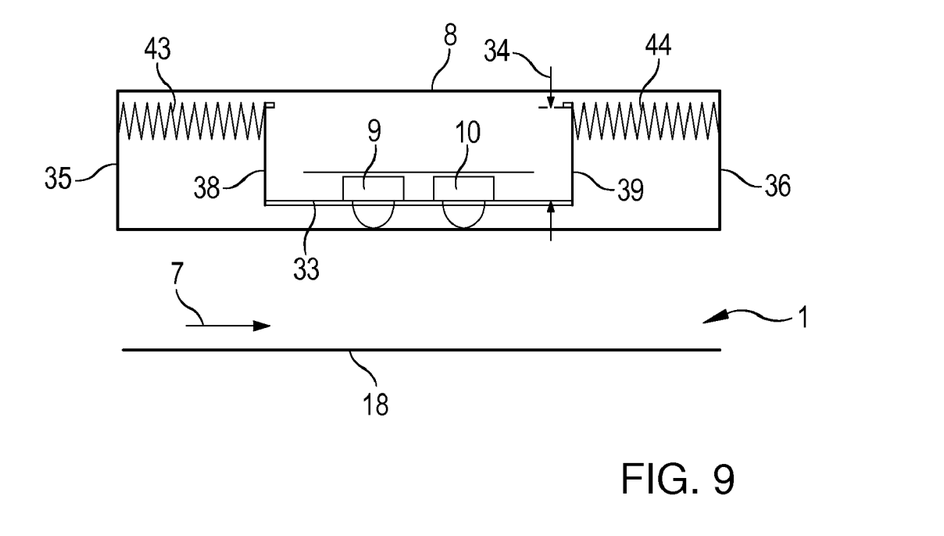
FIG. 9 shows a fifth exemplary embodiment of the erasing apparatus according to the invention with a reflector which has structured reflector surfaces with a plurality of small triangles.

FIG. 9 shows a fifth exemplary embodiment of the erasing apparatus 1 according to the invention. The support 18, above which the holding plane 7 for holding and moving the storage phosphor plate 3 is located, is illustrated. The erasing apparatus 1 contains the reflector 11. The latter has two reflector surfaces 43 and 44, which extend parallel to the holding plane 7 and the support 18 and are disposed to either side of the base 33. The reflector surfaces 43, 44 each have a structure that is substantially triangular in form here, similar to fine saw teeth. By means of this structure, a retroreflective profile of the reflector surfaces 43, 44 is created. This means that the retroreflective reflector surfaces 43, 44 advantageously reflect back at least part of the erasing radiation at points of the storage phosphor layer at which they were previously reflected by the storage phosphor layer. The base 33 is disposed closer to the holding plane 7 than the reflector surfaces 43, 44. The distance 34 between the base 33 and the reflector surfaces 43, 44 is bridged by the connection surfaces 38 and 39.

Figure 10:
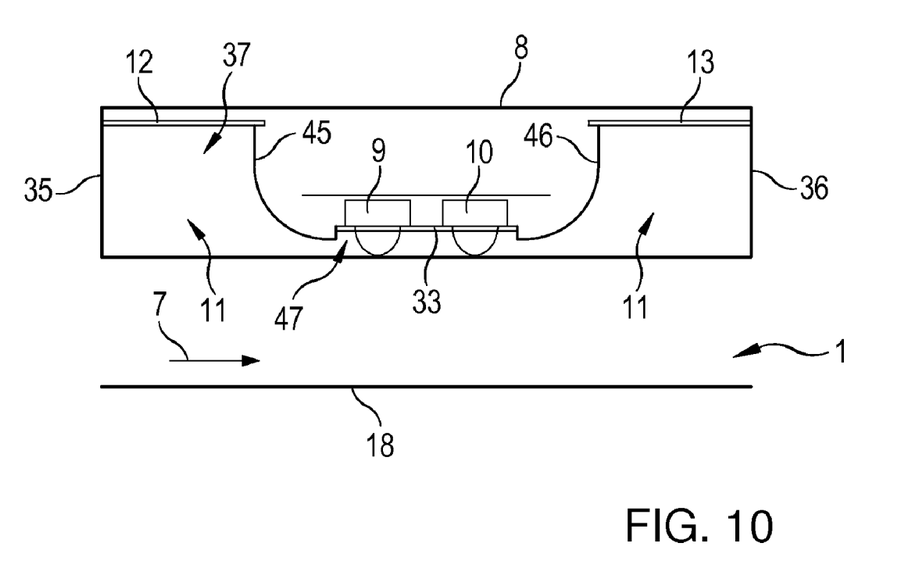
FIG. 10 shows a sixth exemplary embodiment of the erasing apparatus according to the invention with a reflector which has level reflector surfaces and a base for the storage phosphor layer curved in the direction of the holding plane.

FIG. 10 shows a sixth exemplary embodiment of the erasing apparatus 1 according to the invention. Here, the reflector 11, like that of the first exemplary embodiment according to FIG. 1, has the level reflector surfaces 12, 13 that are disposed to either side of the base 33. The base 33 is disposed closer to the holding plane 7 than the reflector surfaces 12, 13. The base 33 is connected to the reflector surfaces 12, 13 by connection surfaces 45 and 46. Unlike the level and vertically extending connection surfaces 38, 39 of the first exemplary embodiment according to FIG. 1, the connection surfaces 45, 46 are curved in the direction of the holding plane 7. Moreover, the two lines of light emitting diodes 9, 10 are positioned in an indentation or recess 47 in the base 33. In this way, the lines of light emitting diodes 9, 10 are particularly well protected from being erasing radiation reflected into them.

Figure 11:
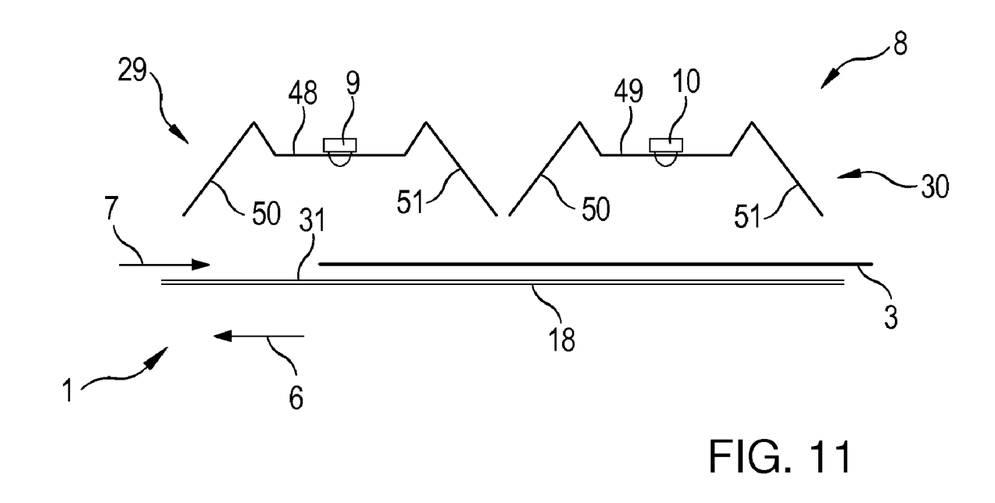
FIG. 11 shows a seventh exemplary embodiment of the erasing apparatus according to the invention with two lines of light emitting diodes which emit light in different wavelength ranges and each have their own reflector.

FIG. 11 shows a seventh exemplary embodiment of the erasing apparatus 1 according to the invention into which the storage phosphor plate 3 is inserted. In this seventh exemplary embodiment the radiation source 8 includes the two lines of light emitting diodes 9, 10, which have their own reflectors and are disposed on bases separated from one another. The line of light emitting diodes 9 is disposed on a base 48 and integrated into a reflector 29. The line of light emitting diodes 10 is disposed on a base 49 and integrated into a reflector 30. The two bases 48, 49 and the two reflectors 29, 30 are spaced apart and separated from one another in the direction of conveyance 6. In this way the erasing radiation emitted by the lines of light emitting diodes 9, 10 hits the storage phosphor layer 2 located in the erasing apparatus 1 separately.

The lines of light emitting diodes 9, 10 emit erasing radiation in different wavelength ranges. The line of light emitting diodes 9 emits erasing radiation in the blue wavelength range, and the line of light emitting diodes 10 in the red wavelength range. In this way good "color separation" and so a high level of erasing efficiency can advantageously be achieved.

Therefore, in the direction of conveyance 6 of the storage phosphor plate 3 first of all blue and then red erasing radiation hits the storage phosphor layer 2. Furthermore, the intensity of the long wavelength or longwave, red erasing radiation is greater than the intensity of the short wavelength or shortwave, blue erasing light.

The intensity portion of the red erasing radiation is advantageously approx. 66% here, and the intensity portion of the blue erasing light is approx. 33%. In this way particularly good erasing efficiency is guaranteed.

The reflectors 29, 30 each have reflector surfaces 50 and 51 that are disposed to either side of the bases 48, 49. The reflector surfaces 50, 51 are of a form that substantially corresponds to an isosceles triangle. The short side of this triangular form adjoins the respective base 48, 49 and extends outwards away from the holding plane 7 at an angle. The long side of this triangular form extends outwards at an angle from the intersection point with the short side in the direction of the holding plane 7. In this way the triangular reflector surfaces 50, 51 are open in the direction of the holding plane 7. The intersection points of the short sides with the long sides of the reflector surfaces 50, 51 are further away from the holding plane 7 than the bases 48, 49 extending parallel to the holding plane 7. The bases 48, 49 are therefore disposed closer to the holding plane 7 than a part of the reflectors 29, 30.

In one preferred variation of this embodiment provision is made such that the inner reflector surfaces 51 and 50 of the two reflectors 29 and 30 which face towards one another extend more steeply, i.e. enclose a smaller angle in relation to the perpendicular, onto the storage phosphor plate 3 than the outer reflector surfaces 50 and 51 facing away from one another. In this way particularly good "color separation" and so a particularly high level of erasing efficiency is achieved.

While this invention has been particularly shown and described with references to preferred embodiments thereof, it will be understood by those skilled in the art that various changes in form and details may be made therein without departing from the scope of the invention encompassed by the appended claims.

What is claimed is:

1. An apparatus for erasing a storage phosphor layer, comprising:
   a holding plane in which the storage phosphor layer lies or is moved,
   a radiation source for irradiating the storage phosphor layer with erasing radiation that is suitable for erasing the storage phosphor layer,
   a base in which the radiation source is positioned and to which the radiation source is attached, the base extending in a direction that is parallel to the holding plane, and a reflector for reflecting erasing radiation in the direction of the holding plane, the reflector being arranged to reflect back erasing radiation that is reflected by the storage phosphor layer in the direction of the storage phosphor layer, wherein the base is positioned closer to the holding plane than at least part of the reflector.

2. The apparatus according to claim 1, wherein the base is reflective in the direction of the holding plane.

3. The apparatus according to claim 1, wherein the reflector is curved in the direction of the holding plane.

4. The apparatus according to claim 1, wherein the base has at least one indentation in which the radiation source is positioned.

5. The apparatus according to claim 1, wherein the base is positioned closer than the whole reflector to the holding plane.

6. The apparatus according to claim 1, wherein the reflector has a reflector surface curving away from the holding plane.

7. The apparatus according to claim 1, wherein the reflector has a flat reflector surface that extends parallel to the holding plane.

8. The apparatus according to claim 1, wherein the reflector has a reflector surface with a structure.

9. The apparatus according to claim 8, wherein the structured reflector surface is retroreflective to reflect back the erasing radiation to points of the storage phosphor layer from which the erasing radiation was previously reflected by the storage phosphor layer.

10. The apparatus according to claim 1, further comprising a drive for producing relative movement between the holding plane and the radiation source.

11. The apparatus according to claim 10, wherein the reflector has at least two reflector surfaces on either side of the radiation source.

12. The apparatus according to claim 11, wherein the reflector is formed mirror-symmetrically in the direction of the relative movement, an axis of symmetry extending at right angles to the direction of the relative movement and, when considered in the direction of the relative movement, centrally through the radiation source.

13. The apparatus according to claim 10, wherein a width of the reflector in the direction of the relative movement is at least ten times as great as a smallest distance between the reflector and the holding plane.

14. The apparatus according to claim 10, wherein the radiation source has at least two lines with light emitting diodes extending at right angles to the direction of the relative movement and parallel to the holding plane.

15. The apparatus according to claim 14, wherein the at least two lines with light emitting diodes are integrated into the base and a distance between the at least two lines is smaller than or equal to a distance between the light emitting diodes and the holding plane.

16. The apparatus according to claim 14, further comprising a particular reflector and a particular base respectively allocated to the at least two lines with light emitting diodes, and the light emitting diodes of the respective lines emit radiation in particular in a narrow-band wavelength range different to that of the light emitting diodes of the other lines.

17. The apparatus according to claim 16, wherein the at least two lines with light emitting diodes are positioned one behind the other in the direction of the relative movement such that when implementing the relative movement in order to erase the storage phosphor layer, shorter wavelength erasing radiation hits the storage phosphor layer before longer wavelength erasing radiation.

18. The apparatus according to claim 16, wherein an intensity of the longer wavelength erasing radiation is greater than an intensity of the shorter wavelength erasing radiation.

19. The apparatus according to claim 18, further comprising a further reflecting surface positioned opposite the reflector, as considered in the direction at right angles to the direction of the relative movement, for reflecting erasing radiation.

20. The apparatus according to claim 19, wherein the further reflecting surface is positioned on the side of the holding plane facing away from the reflector.

21. The apparatus according to claim 1, wherein front surfaces and/or side surfaces of the reflector are reflective.

22. A system, comprising:
a storage phosphor layer; and
an apparatus for erasing the storage phosphor layer, comprising:
a holding plane in which the storage phosphor layer lies or is moved,
a radiation source for irradiating the storage phosphor layer with erasing radiation that is suitable for erasing the storage phosphor layer,
a base in which the radiation source is positioned and to which the radiation source is attached, the base extending in a direction that is parallel to the holding plane, and
a reflector for reflecting erasing radiation in the direction of the holding plane, the reflector being arranged to reflect back erasing radiation that is reflected by the storage phosphor layer in the direction of the storage phosphor layer,
wherein the base is positioned closer to the holding plane than at least part of the reflector.

23. The system according to claim 22, wherein the storage phosphor layer has a degree of reflection for the erasing radiation of greater than or equal to 70%.

24. The system according to claim 22, wherein the storage phosphor layer has a degree of reflection for the erasing radiation of greater than or equal to 80%.

25. A method for erasing a storage phosphor layer, comprising:
defining a plane in which the storage phosphor layer lies or is moved,
with a radiation source, irradiating the storage phosphor layer with erasing radiation that is suitable for erasing the storage phosphor layer,
installing the radiation source in a base, the base extending in a direction that is parallel to the plane,
reflecting erasing radiation in the direction of the holding plane with a reflector, the reflector being arranged to reflect back erasing radiation that is reflected by the storage phosphor layer in the direction of the storage phosphor layer, and
locating the base closer to the holding plane than at least part of the reflector.

26. The method according to claim 25, wherein the reflector has a flat reflector surface that extends parallel to the plane.

* * * * *

UNITED STATES PATENT AND TRADEMARK OFFICE
CERTIFICATE OF CORRECTION

PATENT NO.          : 7,507,984 B2
APPLICATION NO. : 11/831224
DATED                  : March 24, 2009
INVENTOR(S)         : Andreas Bode et al.

It is certified that error appears in the above-identified patent and that said Letters Patent is hereby corrected as shown below:

On the Title Page, item (75) Inventors, at line 4, after Stefan Stallmeister, delete "Gionn" and insert --Glonn--.

Signed and Sealed this

Second Day of June, 2009

JOHN DOLL
*Acting Director of the United States Patent and Trademark Office*